(12) United States Patent
Meftah

(10) Patent No.: US 11,510,739 B2
(45) Date of Patent: Nov. 29, 2022

(54) SYSTEM AND METHOD FOR MEDICAL OBJECT TRACKING

(71) Applicant: CAIRA Surgical, New York, NY (US)

(72) Inventor: Morteza Meftah, New York, NY (US)

(73) Assignee: CAIRA SURGICAL, New York, NY (US)

( * ) Notice: Subject to any disclaimer, the term of this patent is extended or adjusted under 35 U.S.C. 154(b) by 0 days.

(21) Appl. No.: 17/068,978

(22) Filed: Oct. 13, 2020

(65) Prior Publication Data

US 2021/0077199 A1    Mar. 18, 2021

Related U.S. Application Data

(63) Continuation of application No. 17/017,015, filed on Sep. 10, 2020, which is a continuation-in-part of application No. 16/573,095, filed on Sep. 17, 2019.

(51) Int. Cl.
   *A61B 34/20* (2016.01)
   *A61B 34/10* (2016.01)
   *A61B 90/00* (2016.01)

(52) U.S. Cl.
   CPC ........ *A61B 34/20* (2016.02); *A61B 2034/108* (2016.02); *A61B 2034/2051* (2016.02);
   (Continued)

(58) Field of Classification Search
   CPC ............ A61B 34/20; A61B 2034/2051; A61B 2090/3916; A61B 2090/3975; A61B 2090/3991; A61B 2034/108
   See application file for complete search history.

(56) References Cited

U.S. PATENT DOCUMENTS

| 5,604,485 A | 2/1997 | Lauro et al. |
| 7,549,960 B2 | 6/2009 | Govari |

(Continued)

FOREIGN PATENT DOCUMENTS

| EP | 2996555 A2 | 3/2016 |
| WO | 2008063249 A2 | 5/2008 |

(Continued)

OTHER PUBLICATIONS

Merkl, Brandon C., "The Future of the Operating Room: Surgical Preplanning and Navigation Using High Accuracy Ultra-Wideband Positioning and Advanced Bone Measurement." University of Tennesse, Knoxville, Dec. 2008.

(Continued)

*Primary Examiner* — Sanjay Cattungal
(74) *Attorney, Agent, or Firm* — MH2 Technology Law Group, LLP

(57) ABSTRACT

According to one aspect of the invention, a system for medical object tracking is provided. The system includes a plurality of radio frequency transceivers where each of the plurality of radio frequency transceivers are configured to emit a radio frequency signal at a respective frequency. The system includes a radio frequency beacon removably attachable to a medical object where the radio frequency beacon configured to: reflect the radio frequency signals from the plurality of radio frequency transceivers, and emit vibration-based signals. The system includes a control device in communication with the plurality of radio frequency transceivers where the control device includes processing circuitry configured to determine a location of the medical object in three-dimensional space based at least in part on the reflected radio frequency signals and vibration-based signals.

19 Claims, 7 Drawing Sheets

(52) U.S. Cl.
CPC ............... *A61B 2090/3916* (2016.02); *A61B 2090/3975* (2016.02); *A61B 2090/3991* (2016.02)

(56) References Cited

U.S. PATENT DOCUMENTS

| | | | |
|---|---|---|---|
| 7,783,099 B1 | 8/2010 | Stefan et al. | |
| 8,717,430 B2 | 5/2014 | Simon et al. | |
| 9,220,570 B2 | 12/2015 | Kim et al. | |
| 9,467,118 B2 | 10/2016 | Zhou | |
| 9,498,647 B2 | 11/2016 | Kantrowitz et al. | |
| 10,205,238 B1 | 2/2019 | Wurmfeld | |
| 2002/0107445 A1 | 8/2002 | Govari | |
| 2002/0143320 A1 | 10/2002 | Levin | |
| 2004/0068187 A1 | 4/2004 | Krause et al. | |
| 2006/0094958 A1* | 5/2006 | Marquart | A61B 90/36 600/434 |
| 2007/0197891 A1* | 8/2007 | Shachar | A61B 34/73 600/374 |
| 2007/0225595 A1 | 9/2007 | Malackowski et al. | |
| 2008/0154389 A1 | 6/2008 | Smith et al. | |
| 2009/0005708 A1* | 1/2009 | Johanson | A61B 5/6846 600/587 |
| 2010/0085156 A1 | 4/2010 | Tucker | |
| 2010/0137712 A1 | 6/2010 | Krag et al. | |
| 2011/0180609 A1 | 7/2011 | Sato et al. | |
| 2013/0172907 A1* | 7/2013 | Harris | A61B 90/11 606/130 |
| 2014/0200621 A1* | 7/2014 | Malackowski | A61B 34/20 606/86 R |
| 2015/0196369 A1 | 7/2015 | Glossop | |
| 2016/0360997 A1* | 12/2016 | Yadav | A61B 5/1072 |
| 2016/0361101 A1* | 12/2016 | Moctezuma de la Barrera | A61B 17/8028 |
| 2017/0095294 A1 | 4/2017 | Gantes | |
| 2017/0143494 A1 | 5/2017 | Mahfouz | |
| 2017/0239013 A1 | 8/2017 | Frame et al. | |
| 2017/0312035 A1 | 11/2017 | May et al. | |
| 2018/0310830 A1 | 11/2018 | Baldauf et al. | |
| 2019/0192072 A1* | 6/2019 | Bailey | A61B 5/0024 |
| 2019/0350518 A1* | 11/2019 | Bailey | A61B 5/0024 |
| 2019/0380792 A1* | 12/2019 | Poltaretskyi | G06N 3/0454 |
| 2020/0000366 A1 | 1/2020 | Katabi et al. | |
| 2020/0138518 A1 | 5/2020 | Lang | |
| 2020/0163044 A1 | 5/2020 | Bapat et al. | |
| 2020/0170751 A1 | 6/2020 | Pack et al. | |
| 2020/0237441 A1* | 7/2020 | Zuhars | A61B 34/20 |
| 2020/0405440 A1 | 12/2020 | Shelton, IV et al. | |
| 2021/0038328 A1 | 2/2021 | Boisvert et al. | |
| 2021/0077198 A1 | 3/2021 | Meftah | |
| 2021/0080563 A1 | 3/2021 | Meftah | |
| 2021/0153946 A1 | 5/2021 | Bonny et al. | |

FOREIGN PATENT DOCUMENTS

| | | |
|---|---|---|
| WO | 2011136986 A1 | 11/2011 |
| WO | 2016199051 A1 | 12/2016 |
| WO | 2017185170 A1 | 11/2017 |

OTHER PUBLICATIONS

Growshapes Biomedical Case Study. http://www.growshapes.com/uploads/2/5/6/0/25608031/casestudy_biomedical (May 2015).

Staff News Brief, "White Light Scanner—Alternative to CT for Assessment of Pediatric Chest Deformities" http://appliedradiology.com/articles/white-light-scanner-alternative-to-ct-for-assessment-of-pediatric-chest-deformities (Jun. 7, 2016).

Vorum, Medical Expo, http://www.medicalexpo.com/prod/vorum/product-104119-761593.html (Last viewed Jan. 28, 2019).

https://www.youtube.com/watchv=ibkmvfoN8LY. 3D Scan: Knee Scan With BodyScan (Published on Dec. 3, 2014; Last viewed Jan. 28, 2019).

Pecheva et al., "White Light Scanning Interferometry Adapted For Large-Area Optical Analysis of Thick and Rough Hydroxyapatite Layers." https://www.ncbi.nlm.nih.gov/pubmed/17295521 (Mar. 27, 2007; Epub Feb. 13, 2007).

3D Bone Models by CinZara. https://www.cinzara.com/services/3d-bone-models/ Copyright 2017 (Last viewed on Jan. 28, 2019).

Thomas et al., "3D Printing for Reconstructive Surgery." Woodhead Publishing Series in Biomaterials. (https://books. google.com/booksid=tEiZDgAAQBAJ pg=PA42 lpg=PA42 dq=white+light+scanner+surgery source=bl ots=jBlgjUGWgt sig=uQ4ZVNx9AJoEFjSv3EOx5gMiDBI hl=en sa=X ved=OahUKEwiVzLDOOc7YAhVCO2MKHbyhBNOQ6AEllgEwDQ#v=onepage q=white%20light%20scanner%20surgery f=false) (2018).

Office Action issued in U.S. Appl. No. 16/254,220 dated Feb. 25, 2021, 14 pages.

Notice of Allowance issued in U.S. Appl. No. 16/254,220 dated Jul. 1, 2021, 7 pages.

Office Action issued in U.S. Appl. No. 16/573,095 dated Jul. 30, 2021, 16 pages.

Office Action issued in U.S. Appl. No. 17/017,015 dated Oct. 27, 2021, 29 pages.

International Search Report and Written Opinion issued in International Patent Application No. PCT/US2021/021863 dated Sep. 6, 2021, 20 pages.

Office Action issued in U.S. Appl. No. 16/573,095 dated Jun. 2, 2022, 26 pages.

Office Action issued in U.S. Appl. No. 16/573,095 dated Sep. 15, 2022, 13 pages.

\* cited by examiner

SYSTEM AND METHOD FOR MEDICAL OBJECT TRACKING

CROSS-REFERENCE TO RELATED APPLICATION

This application is a continuation of U.S. application Ser. No. 17/017,015 filed Sep. 10, 2020, which is a continuation-in-part and claims priority to U.S. patent application Ser. No. 16/573,095, filed on Sep. 17, 2019, entitled SYSTEM AND METHOD FOR MEDICAL OBJECT TRACKING, the entirety of which is incorporated herein by reference.

FIELD

The present technology is generally related to location monitoring of objects in a medical environment.

BACKGROUND

Placement of implants in bones or soft tissue requires precise planning. For example, in joint replacement orthopedic surgery, precise bony cuts are essential to achieve optimum outcomes. In order to achieve this, historically manual cutting blocks that reference boney landmarks, limb anatomical alignment, and visual cues have been designed to help the surgeon place the guides; however, these guides lack the necessary precision due to inherent issues with manual cutting jigs.

In recent years utilizing computed assisted surgery (CAS), such as navigation and robots, have been developed to improve the accuracy of implant positioning. Existing CAS systems may require optical trackers for the computer to identify bones that are in constant movement during surgery. These optical trackers include multiple large pins that need to be fixed into each bone, most of the time through separate incisions, that may cause fractures and more pain for the patients. Further, these optical trackers may need a bulky optical apparatus that requires a line of sight for a camera, and large amount of hardware and software to operate. Moreover, there is no systematic way to adjust the implant position based on the patients' individual soft-tissue tension. Most CAS are tailored to achieve a "balanced" soft tissue by surgeons' manual tests. These manual techniques are not accurate or reproducible since the human anatomy varies.

Radar technology, used widely in various industries, utilizes pulsed sound waves at various frequencies to track the distance and speed of an object based on the return of the signal and its modified frequency. Therefore, an object travelling away from the radar source would return a longer wavelength, and an object travelling towards the source would return a shorter wavelength. There are current radar application available in automobile and defense industry that aim to achieve high precision location. One such radar is commercially available, operating at 77 GHZ with wide 4 GHZ bandwidth that allows for high resolution and accuracy with the use of FMCW radar. However, there are no applications available to achieve a resolution below one millimeter in short range.

In an operating room (OR), radar sources can be used to triangulate the location of an object that returns waves more efficiently than the surrounding objects. Furthermore, varying the frequency of the waves emitted by the sources can allow the positioning of the object to be more accurate. If the object positional accuracy is required to be sub-millimeter, we would need waves of multiple wavelengths to determine the true location so that the object's location that may be in between the wavelengths is not misjudged. Submillimeter is defined as 1 um-1 mm accuracy (micrometer-millimeter).

Therefore, existing systems suffer from one or more issues.

SUMMARY

The techniques of this disclosure generally relate to objection location monitoring in a medical environment.

The techniques of this disclosure a system for the precise tracking of an area of interest comprising one or more radiofrequency (RF) transceivers and one or more active very small beacons that emit radio frequency or vibration-based signals in short- to mid-range distances. These novel beacons will actively re-transmit the frequency-shifted radar signals after initial receiving. Since each beacon imposes a unique frequency shift to the incoming radar signal, exhibiting specific Doppler frequencies, the location can be measured with less than one millimeter accuracy. These active beacons are designed to achieve high accuracy, increase the signal to noise ratio, with a small size (less than 1 inch) that can be disposable and also be used with off-the-shelf batteries.

Object triangulation: Three primary radars in equidistant locations from the region of interest tracking, for example bone tracking for orthopaedic applications and tool tracking, for example a bone saw for orthopaedic applications. The three radars emit waves at varying frequencies in pulses of milliseconds so each returning wave will be from a different frequency. A calibration device will be used to determine how sub millimeter differences affect each change in distance. During surgery, a laser range finder will be also attached to the radars to determine true distance from the radars prior to the surgery. Once the ranges are set, wavelengths of appropriate frequency will be used for that range of distance to yield the most accurate readings for the tools and bones. Beacons can also be placed on the radar receivers to detect any changes on the radar locations. This method is used to re-calibrate the radars and avoids bias.

A hand-held scanner (such as Laser or LIDAR) that will in turn be tracked by the three radars. This hand-held device will be used to scan the bone surface by bouncing waves from the surface and recording the distance as a laser range finder is again used to find the appropriate wavelength spectrum and to keep track of the scanned areas and how they relate to the new locations as the surgeon moves the device several millimeters or so from and to the joint. This variation will be tracked to stitch all scans together to get the true surface geometry. The scanning device will be tracked in the air with the radars similar to the cutting tools to close the loop of bone location determination.

Once the scan is complete, cutting tools such as the free hand bone saw or a cutting block that helps the surgeon make the cuts can be tracked in the air and placed in the appropriate location to achieve the planned surgery.

The scanner can also be used to make measurements after the cuts to determine the accuracy of the cuts to report back to the surgeon to conduct validation.

In one or more embodiments, the system described herein improves on existing system by simplifying the tracking of the bones such as by using a wave-based technology that can penetrate through objects. This allows for the surgeon to break the line-of-sight without the loss of signal, which may increase the safety of the surgery as the system is always able to track the object(s). Although there might be a temporary drop in signal strength, adding more radar through triangulation will resolve this issue. Also, with specific algorithms that utilize machine learning, the outcomes of prior implant positions can be taken into consideration such that the radar system can suggest a customized position based patient's demographic and severity or deformity of the disease and surgeon's preference.

In one or more embodiments, a radar, i.e., RF, based tracking system is provided where the system utilizes RF beacons that have unique signatures generating Doppler shifted waves, i.e., RF signals, which can be tracked.

A set of radars, static or moving, emit RF signals in the area of interest. The area of interest contains a set of passive or active RF beacons, whose purpose is to re-radiate a clear, unique signal back to the radars so that their three-dimensional position and inclination can be inferred through opportune signal processing.

These RF beacons, disseminated in the area of interest, receive these radar signals, shift their carrier frequencies within prescribed values, and actively re-transmit the frequency-shifted radar signals omnidirectionally. Each beacon imposes a unique frequency shift to the incoming radar signal, thus permitting its identification at the radar receiver after some signal processing. Specifically, these beacon-generated frequency shifts are perceived by the radars as targets exhibiting specific Doppler frequencies.

Through Range-Doppler processing, or similar Moving-Target-Indication techniques, each radar measures the range and Doppler of signal echoes in the area of interest. Echoes exhibiting zero or near-zero Doppler values correspond to clutter, and are removed by the radar signal processor. Echoes corresponding to specific Doppler frequencies associated to the beacon in the area of interest, are isolated, processed and tracked. The actual three-dimensional location of RF beacons is calculated through triangulation of the range information collected across all the radars radiating the area of interest.

A sequence of varying wave frequencies is generated from multiple RF transceivers and by the same sources for doppler shifts to find a unique RF beacon and associated object in a three-dimensional space. A control device may be used to compare the point cloud generated from the measurements against the supervised machine learning dataset to correct for inaccuracies signal processing and/or machine learning. The RF beacon represents both position and orientation with the use of the RF beacon and an accelerometer to identify the position of an object, for example, a bone, when the RF beacon is fixed to it. Any motion of this object is then tracked such as by RF transceivers and/or control device and can be plotted in by control device to allow the user to manipulate the object based on its defined location with external tools. Control device may be configured with augmented reality, and where virtually reality can be overlaid on the tracked object to allow the user to manipulate the object.

According to one aspect of the invention, a system for medical object tracking is provided. The system includes a plurality of radio frequency transceivers where each of the plurality of radio frequency transceivers are configured to emit a radio frequency signal at a respective frequency. The system includes a radio frequency beacon removably attachable to a medical object where the radio frequency beacon configured to: actively modify the radio frequency signals from the plurality of radio frequency transceivers. The system includes a control device in communication with the plurality of radio frequency transceivers where the control device includes processing circuitry configured to determine a location of the medical object in three-dimensional space based at least in part on the reflected radio frequency signals.

In one embodiment, 6 degree of freedom and tilt measurement are obtained through uses accelerometer(s) and/or multiple antennas (2 or more beacon). These multiple antennas can be placed on the same beacon or multiple separate beacons can be placed on the bone or tracking object.

According to one or more embodiments, the include at least one signal generated active RF beacons emit shifted frequencies with or without the vibration based or acoustic signals. According to one or more embodiments, the vibration-based signals include at least one signal based at least in part on a resonant frequency of at least one material of the radio frequency beacon. An active beacon can be vibration based, RF based, or generates doppler frequency through mechanical vibration. According to one or more embodiments, the vibration-based signals are triggered at least in part by receiving at least one of the radio frequency signals from the plurality of radio frequency transceivers.

According to one or more embodiments, the radio frequency beacon includes a conical component, the conical component configured to reflect the radio frequency signals. According to one or more embodiments, the plurality of radio frequency transceivers are configured to interrogate a respective predefined area at a predefined sweep frequency. The control device is configured to modify the respective predefined area and predefined sweep frequency based at least in part on the location of the medical object.

According to one or more embodiments, the medical object is one of a surface of a bone and a medical device. According to one or more embodiments, the determination of the location of the medical object in three-dimensional space includes determining, for each respective reflected radio frequency signal, a respective location in three-dimensional space of the medical object. The determined location of the medical object in three-dimensional space is based on the determined respective locations in three-dimensional space of the medical object.

According to one or more embodiments, the radio frequency beacon includes at least one accelerometer configured to generate accelerometer data. At least one of the reflected radio frequency signals includes the accelerometer data. According to one or more embodiments, the control device is further configured to determine an orientation of the radio frequency beacon in the three-dimensional space based at least in part on the accelerometer data.

According to another aspect of the invention, a method implemented in a system for medical object tracking is provided. A radio frequency signal is emitted at a respective frequency at each radio frequency transceiver of a plurality of radio frequency transceivers. The radio frequency signals are reflected, at a radio frequency beacon removably attachable to the medical object, from the plurality of radio frequency transceivers. Vibration-based signals are emitted at the radio frequency beacon. A location of the medical object in three-dimensional space is determined based at least in part on the reflected radio frequency signals and vibration-based signals.

According to one or more embodiments, the vibration-based signals include at least one signal generated by a haptic device. According to one or more embodiments, the vibration-based signals include at least one signal based at least in part on a resonant frequency of at least one material of the radio frequency beacon. According to one or more embodiments, the vibration-based signals are triggered at least in part by receiving the radio frequency signals from the plurality of radio frequency transceivers.

According to one or more embodiments, the reflected radio frequency signals are reflected by a conical component of the radio frequency beacon. According to one or more embodiments, the emitting, at each radio frequency transceivers, of the radio frequency signal at the respective frequency corresponds to interrogating a respective predefined area at a predefined sweep frequency. The respective predefined area and predefined sweep frequency is modified based at least in part on the reflected radio frequency signals and vibration-based signals.

According to one or more embodiments, the medical object is one of a surface of a bone and a medical device. According to one or more embodiments, the determination of the location of the medical object in three-dimensional space includes determining, for each respective reflected radio frequency signal, a respective location in three-dimensional space of the medical object. The determined location of the medical object in three-dimensional space is based on the determined respective locations in three-dimensional space of the medical object.

According to one or more embodiments, accelerometer data is generated at the radio frequency beacon using at least one accelerometer. The reflected radio frequency signals include the accelerometer data. According to one or more embodiments, an orientation of the radio frequency beacon in the three-dimensional space is determined based at least in part on accelerometer data.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1:
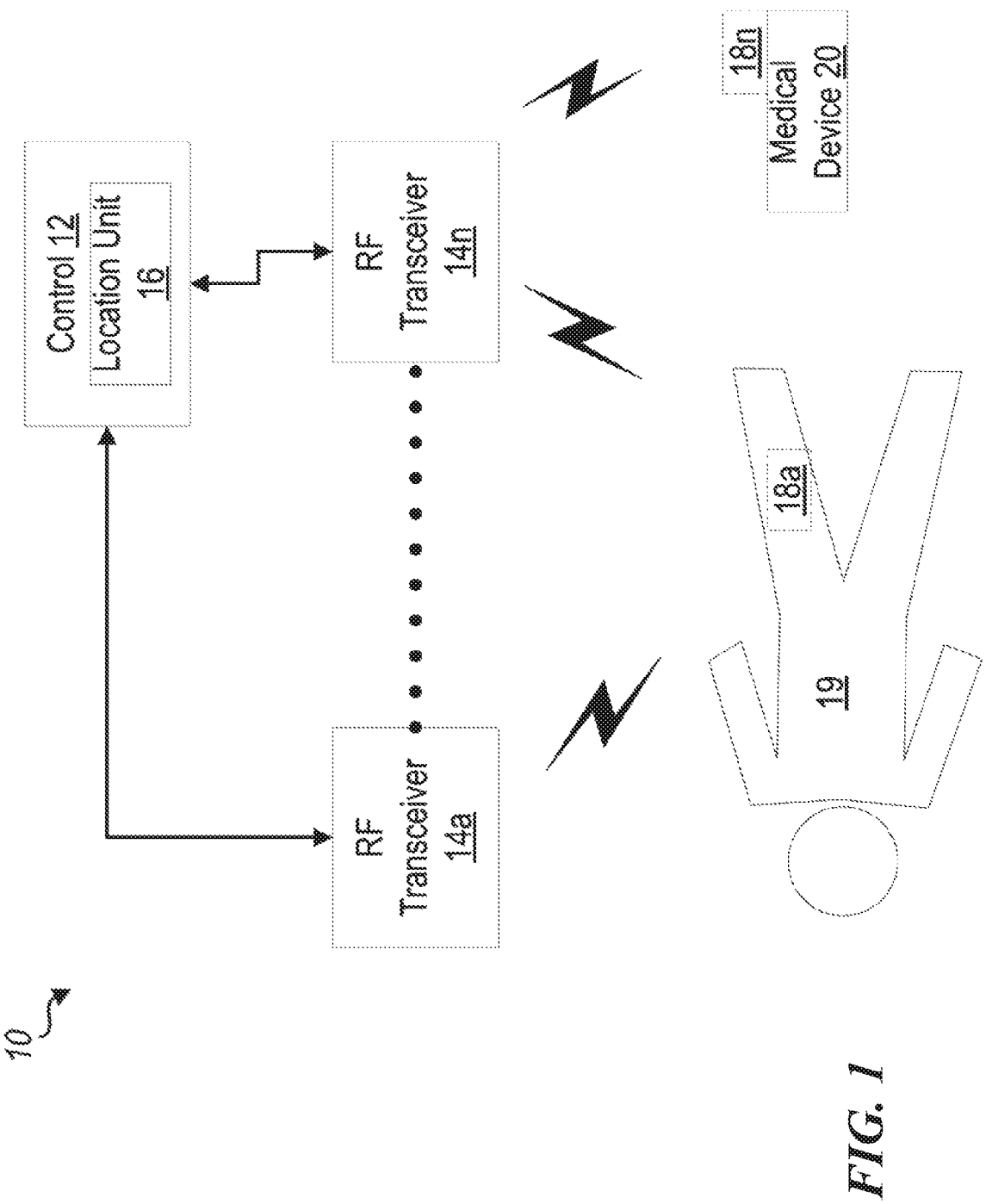
FIG. 1 is a diagram of an example system according to one or more embodiments of the invention.

Before describing in detail exemplary embodiments, it is noted that the embodiments reside primarily in combinations of apparatus components and processing steps related to objection location monitoring. Accordingly, components have been represented where appropriate by conventional symbols in the drawings, showing only those specific details that are pertinent to understanding the embodiments so as not to obscure the disclosure with details that will be readily apparent to those of ordinary skill in the art having the benefit of the description herein. Like numbers refer to like elements throughout the description.

As used herein, relational terms, such as "first" and "second," "top" and "bottom," and the like, may be used solely to distinguish one entity or element from another entity or element without necessarily requiring or implying any physical or logical relationship or order between such entities or elements. The terminology used herein is for the purpose of describing particular embodiments only and is not intended to be limiting of the concepts described herein. As used herein, the singular forms "a", "an" and "the" are intended to include the plural forms as well, unless the context clearly indicates otherwise. It will be further understood that the terms "comprises," "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

In embodiments described herein, the joining term, "in communication with" and the like, may be used to indicate electrical or data communication, which may be accomplished by physical contact, induction, electromagnetic radiation, radio signaling, infrared signaling or optical signaling, for example. One having ordinary skill in the art will appreciate that multiple components may interoperate and modifications and variations are possible of achieving the electrical and data communication.

In some embodiments described herein, the term "coupled," "connected," and the like, may be used herein to indicate a connection, although not necessarily directly, and may include wired and/or wireless connections.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

Referring now to the drawing figures, in which like elements are referred to by like reference numerals, there is shown in FIG. 1 a schematic diagram of a communication system 10, which comprises control device 12 in communication with radio frequency (RF) transceiver 14a-14n (collectively referred to as RF transceiver 14). Control device 12 may include location unit 16 for performing one or more control device 12 functions as described herein such as with respect to object location in a three-dimensional space. System 10 further includes RF beacons 18a-18n (collectively referred to as RF beacon 18) that are configured to communicate one or more signals in response to an interrogation signal from RF transceiver 14 in a medical environment, for example, as described herein. RF beacon 18 may be removably attached and/or inserted into a device or medical object, e.g., pin, that attached a person 19 or patient 19. In one or more embodiments, RF beacon 18 is removably attached/attachable to a medical object such as medical device 20.

Figure 2:
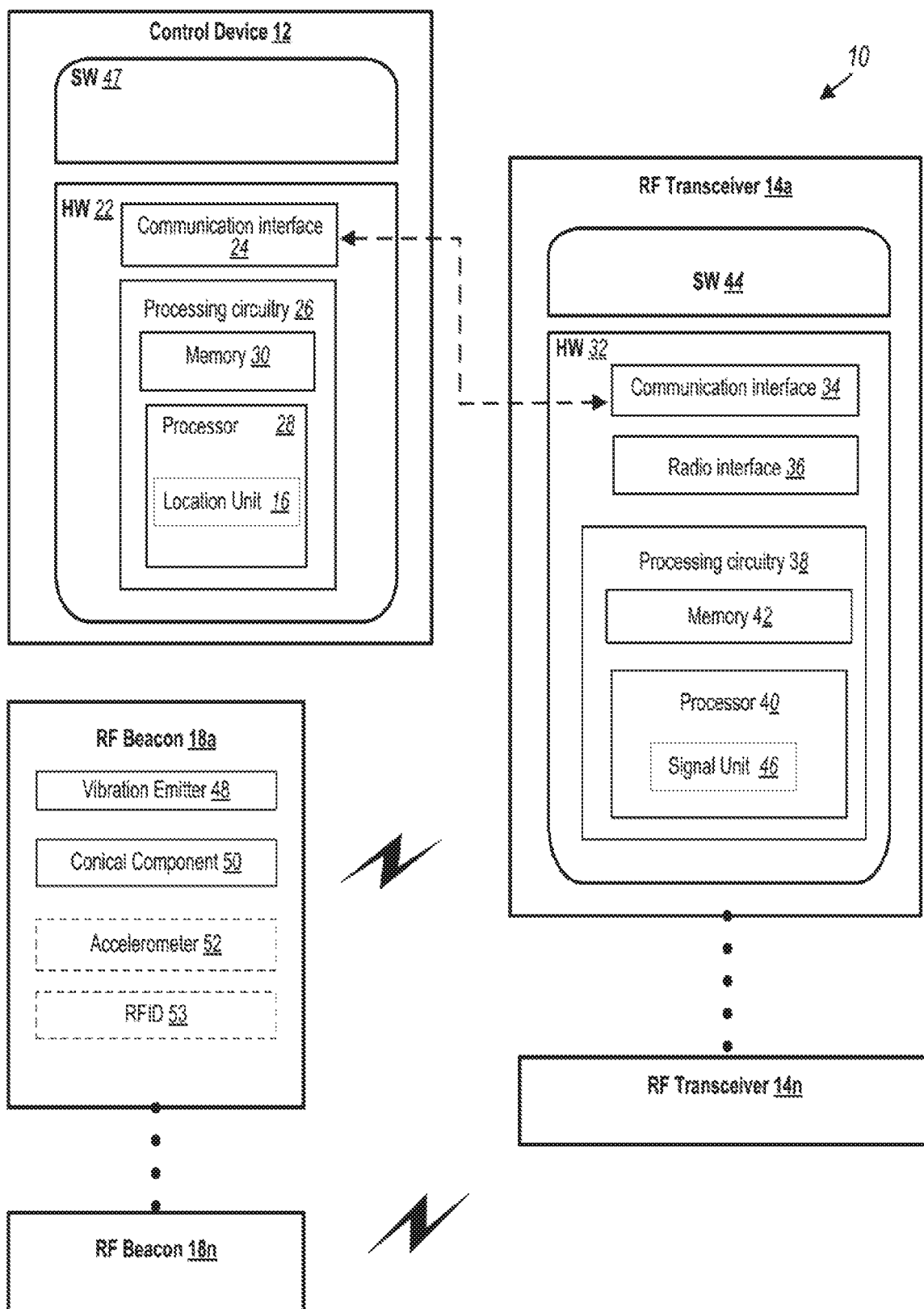
FIG. 2 is block diagram of FIG. 1 according to one or more embodiments of the invention.

FIG. 2 is a block diagram of an example system 10 according to one or more embodiments of the invention. The system 10 includes a control device 12 that includes hardware 22 enabling it to communicate with RF transceivers 14. The hardware 22 may include a communication interface 24 for setting up and maintaining a wired or wireless connection with an interface of a different device such as RF transceiver 14 of the communication system 10.

In the embodiment shown, the hardware 22 of the control device 12 further includes processing circuitry 26. The processing circuitry 26 may include a processor 28 and a memory 30. In particular, in addition to or instead of a processor, such as a central processing unit, and memory, the processing circuitry 26 may comprise integrated circuitry for processing and/or control, e.g., one or more processors and/or processor cores and/or FPGAs (Field Programmable Gate Array) and/or ASICs (Application Specific Integrated Circuitry) adapted to execute instructions. The processor 28 may be configured to access (e.g., write to and/or read from) the memory 30, which may comprise any kind of volatile and/or nonvolatile memory, e.g., cache and/or buffer memory and/or RAM (Random Access Memory) and/or ROM (Read-Only Memory) and/or optical memory and/or EPROM (Erasable Programmable Read-Only Memory).

Thus, the control device 12 further has software stored internally in, for example, memory 30, or stored in external memory (e.g., database, storage array, network storage device, etc.) accessible by the control device 12 via an external connection. The software 47 may be executable by the processing circuitry 26. The processing circuitry 26 may be configured to control any of the methods and/or processes described herein and/or to cause such methods, and/or processes to be performed, e.g., by control device 12. Processor 28 corresponds to one or more processors 28 for performing control device 12 functions described herein. The memory 30 is configured to store data, programmatic software code and/or other information described herein. In some embodiments, the software 47 may include instructions that, when executed by the processor 28 and/or processing circuitry 26, causes the processor 28 and/or processing circuitry 26 to perform the processes described herein with respect to control device 12. For example, processing circuitry 26 of the control device 12 may include location unit 16 configured to perform one or more control device 12 functions as described herein such as with respect to RF beacon location.

The system 10 further includes an RF transceiver 14 provided in a communication system 10 and including hardware 32 enabling it to communicate with the control device 12 and/or RF beacon 18. The hardware 32 may include a communication interface 34 for setting up and maintaining a wired or wireless connection with an interface of different devices of the communication system 10 such as control device 12, as well as a radio interface 36 for wirelessly communicating with RF beacon 18, as described herein. The radio interface 36 may be formed as or may include, for example, one or more RF transmitters, one or more RF receivers, and/or one or more RF transceivers.

In the embodiment shown, the hardware 32 of the RF further includes processing circuitry 38. The processing circuitry 38 may include a processor 40 and a memory 42. In particular, in addition to or instead of a processor, such as a central processing unit, and memory, the processing circuitry 38 may comprise integrated circuitry for processing and/or control, e.g., one or more processors and/or processor cores and/or FPGAs (Field Programmable Gate Array) and/or ASICs (Application Specific Integrated Circuitry) adapted to execute instructions. The processor 40 may be configured to access (e.g., write to and/or read from) the memory 42, which may comprise any kind of volatile and/or nonvolatile memory, e.g., cache and/or buffer memory and/or RAM (Random Access Memory) and/or ROM (Read-Only Memory) and/or optical memory and/or EPROM (Erasable Programmable Read-Only Memory).

Thus, the RF transceiver further has software 44 stored internally in, for example, memory 42, or stored in external memory (e.g., database, storage array, network storage device, etc.) accessible by the RF transceiver 14 via an external connection. The software 44 may be executable by the processing circuitry 38. The processing circuitry 38 may be configured to control any of the methods and/or processes described herein and/or to cause such methods, and/or processes to be performed, e.g., by RF transceiver. Processor 40 corresponds to one or more processors 40 for performing RF transceivers 14 functions described herein. The memory 42 is configured to store data, programmatic software code and/or other information described herein. In some embodiments, the software 44 may include instructions that, when executed by the processor 40 and/or processing circuitry 38, causes the processor 40 and/or processing circuitry 38 to perform the processes described herein with respect to RF transceiver 14. For example, processing circuitry 38 of the RF transceiver 14 may include signal unit 46 configured to perform one or more RF transceivers 14 functions described herein such as with respect to transmitting and/or receiving wireless signals.

System 10 includes one or more RF beacons 18 where each RF beacon 18 may include a vibration emitter 48, conical component 50, and an optional accelerometer 52. In particular, the RF transceivers 14 and control device 12 are tracking a RF beacon 18 that may be removably attached close to the exposed surface of the bone, that does not require separate incisions. The RF beacon 18 is configured to emit vibrations such as via vibration emitter 48 to generate doppler shifts. This vibration-based signal may provide additional interference waves to indicate the RF beacon 18's true location down to sub millimeter accuracy, e.g., 1 millimeter accuracy with an error of less than 1 millimeter. In one or more embodiments, a motor in a device such as surgical saw or drill may act as a vibration emitter 48 and/or an additional vibration emitter 48 where the doppler shifts from the receding and approaching surfaces of the motor blade may be averaged to a single point.

In one or more embodiments, RF beacons 18 may be configured to respond one or more specific frequency of signals transmitted by one or more RF transceivers 14 to reach their resonant frequency. In one or more embodiments, vibration emitter 48 is a resonating element that vibrates in response to the received signals from one or more RF transceivers 14 to generate an additional vibration-based signal that the RF transceivers 14 can detect to refine location accuracy. In one or more embodiments, the RF beacon 18 may at least in part by made from a material that is configured generate the vibration-based signal in response to one or more RF transceiver 14 signals. The vibration-based signal may be the same frequency of the received RF signal or may be a different predefined frequency. In one or more embodiments, the vibration emitter 48 is a passive resonant emitter that starts vibrating when an RF signal at a predefined frequency bounces off it.

In one or more embodiments, vibration emitter 48 is a haptic element that causes vibration in response to the received signals from one or more RF transceivers 14 to generate an additional vibration-based signal that the RF transceivers 14 can detect to refine location accuracy. For example, in one or more embodiments, haptic element rotates at a specific rate in which the RF transceiver 14 can detect and track. RF beacons 18 may rotate by haptic vibration motors which may be coded to rotate/vibrate at specific rates/frequencies. Control device 12 may use specific algorithms coded into software 47 to be able to filter through ambient noise and focus directly on the vibration/rotation of the RF beacon 18 such as by using, for example, doppler filtering. In one or more embodiments, doppler filtering allows for the detection of weak signals in the presence of strong clutter by, for example, differentiating moving and static signatures.

Accelerometers 52 may be used to detect and monitor the vibration of the RF beacon 18 and provide instantaneous feedback of the X, Y and Z coordinates to control device 12 for real-time tracking. For example, in a single accelerometer/gyro 52 combination, pitch roll yaw can be determined for orienting RF beacon 18 in 3D space. The data from accelerometer 52 may be transmitted to control device 12 via one or more wireless communication protocols via a radio interface of RF beacon by which control device can determine a point location of RF beacon 18 and accelerometer orientation for plane. The plane may define the bone or other medical object orientation with respect to RF transceivers 14. The wireless communication protocols may include BLUETOOTH.

In one or more embodiments, conical component 50 is configured to reflect radar waves, i.e., RF signals from one or more RF transceivers 14, in an efficient path back to one or more RF transceivers 14. For example, the conical component 50 may be an active device that spins to reflect the RF signals from RF transceiver 14. In one or more embodiments, the spinning of the conical component 50 may be triggered by receiving the RF signal and/or may spin periodically or continuously while powered. In one or more embodiments, RF beacon 18 may include a radio frequency identification (RFID) that may be embedded on the reflected signal and/or RFID may generate a separate RF signal indicating the RFID.

In one or more embodiments, the one or more frequencies used herein may be modified to keep the RF beacons 18 within a predefined band. The system 10 may be calibrated with other frequency generators such as a saw or drill at least in part by determining the unique signal signatures for these devices or frequency generators. The software described herein may filter these frequencies and assign unique frequencies to the beacons to prevent noise generation. Once the system uniquely identifies the RF beacons 18, the location and/or position of the RF beacons 18 may be used for determining final implant placement, for example.

Figure 3:
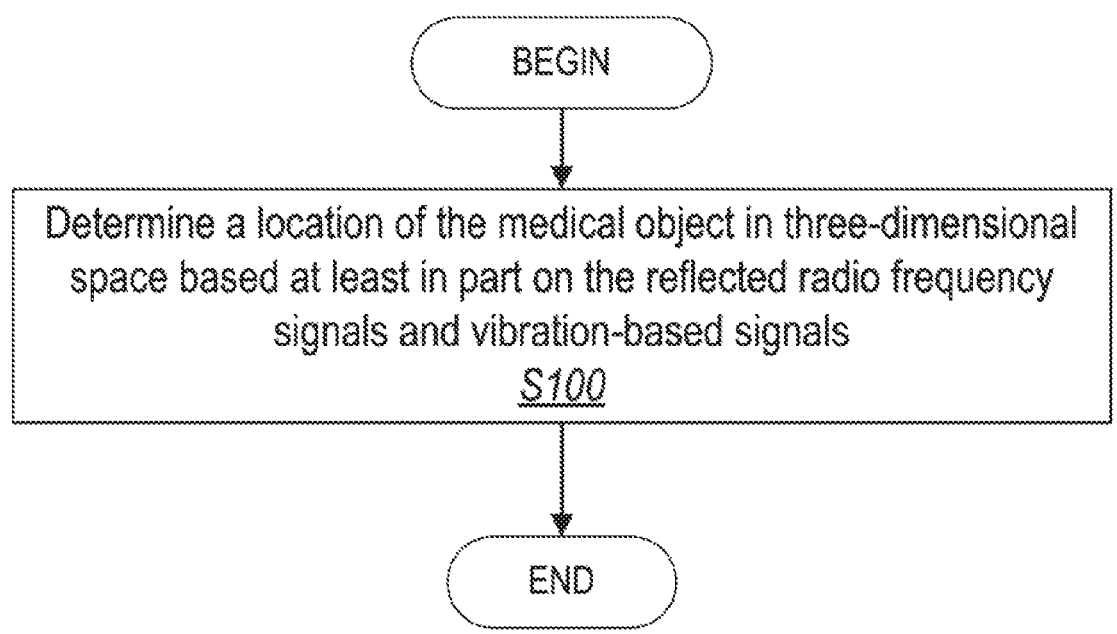
FIG. 3 is a flow diagram of an example process according to one or more embodiments of the disclosure.

FIG. 3 is an example flowchart of a process of control device 12 according to one or more embodiments of the invention. One or more Blocks and/or functions performed by control device 12 may be performed by one or more elements of control device 12 such as by location unit 16, processing circuitry 26, processor 28, etc. In one or more embodiments, control device 12 such as via one or more of location unit 16, processing circuitry 26, processor 28, etc. is configured to determine (Block S100) a location of the medical object in three-dimensional space based at least in part on the reflected radio frequency signals and vibration-based signals. For example, in one or more embodiments, a system 10 for medical object tracking is provided where the system 10 includes a plurality of radio frequency transceivers 14. Each of the plurality of radio frequency transceivers 14 are configured to emit a radio frequency signal at a respective frequency such as to interrogate a predefined area for RF beacons 18, for example. In one or more embodiments, one or more radio frequency transceivers 14 is configured to scan an entire surgery area, i.e., predefined area, for signals originating from one or more beacons 18.

System 10 includes a radio frequency beacon 18 that is removably attachable to a medical object where the radio frequency beacon configured to: reflect the radio frequency signals from the plurality of radio frequency transceivers such as via conical component 50; and emit vibration-based signals such as via vibration emitter 48. In one or more embodiments, the reflected radio frequency signals and the vibration-based signals are detected by one or more of the radio frequency transceivers 14. System 10 further includes a control device 12 in communication with the plurality of radio frequency transceivers 14 where the control device 12 includes processing circuitry 38 configured to determine (Block S100) a location of the medical object in three-dimensional space based at least in part on the reflected radio frequency signals and vibration-based signals.

According to one or more embodiments, the vibration-based signals include at least one signal generated by a haptic device. According to one or more embodiments, the vibration-based signals include at least one signal based at least in part on a resonant frequency of at least one material of the radio frequency beacon 18. According to one or more embodiments, the vibration-based signals are triggered at least in part by receiving at least one of the radio frequency signals from the plurality of radio frequency transceivers 14.

According to one or more embodiments, the radio frequency beacon includes a conical component 50 where the conical component 50 is configured to reflect the radio frequency signals. According to one or more embodiments, the plurality of radio frequency transceivers 14 are configured to interrogate a respective predefined area at a predefined sweep frequency where the control device 12 is configured to modify the respective predefined area and predefined sweep frequency based at least in part on the location of the medical object.

According to one or more embodiments, the medical object is one of a surface of a bone and a medical device. According to one or more embodiments, the determination of the location of the medical object in three-dimensional space includes determining, for each respective reflected radio frequency signal, a respective location in three-dimensional space of the medical object. The determined location of the medical object in three-dimensional space is based on the determined respective locations in three-dimensional space of the medical object.

According to one or more embodiments, the radio frequency beacon 18 includes at least one accelerometer 52 configured to generate accelerometer data where at least one of the reflected radio frequency signals including the accelerometer data. According to one or more embodiments, the control device 12 is further configured to determine an orientation of the radio frequency beacon 18 in the three-dimensional space based at least in part on the accelerometer data.

In one or more embodiments, pulsed waves, i.e., RF signals, at various frequencies, for example, 3 to 300 GHz, are transmitted by RF transceiver 14 such as via radio interface 36 to track the distance and speed of an object based on the return of the signal and its modified frequency. Such changes in frequency response can be identified, characterized, and classified as unique signals such as by RF transceiver 14 and/or control device 12. In one or more embodiments, RF transceivers 14 can be used to triangulate the location of an RF beacon 18 that returns waves more efficiently than the surrounding objects. In one or more embodiments, the RF transceivers 14 may triangulate the location of the RF beacon based at least in part on the vibration-based signals from vibration emitter 48 of RF beacon 18, where the results of the object triangulation for the various signals (e.g., reflected radio frequency signals and vibration-based signals) can be combined or processed such as, for example, into a final waveform such as, for example, via Fourier transform.

In other configuration, no vibration-based signals are transmitted and the Doppler shifts are achieved by an active beacon 18 discussed in more detail below. Furthermore, varying the frequency of the waves emitted by the RF transceivers 14 can allow the positioning of the object to be more accurate. If the object's positional accuracy is required to be sub-millimeter, waves of multiple wavelengths may be used by control device 12 to determine the location so that the object's location that may be in between the wavelength may not be misjudged.

Figure 4:
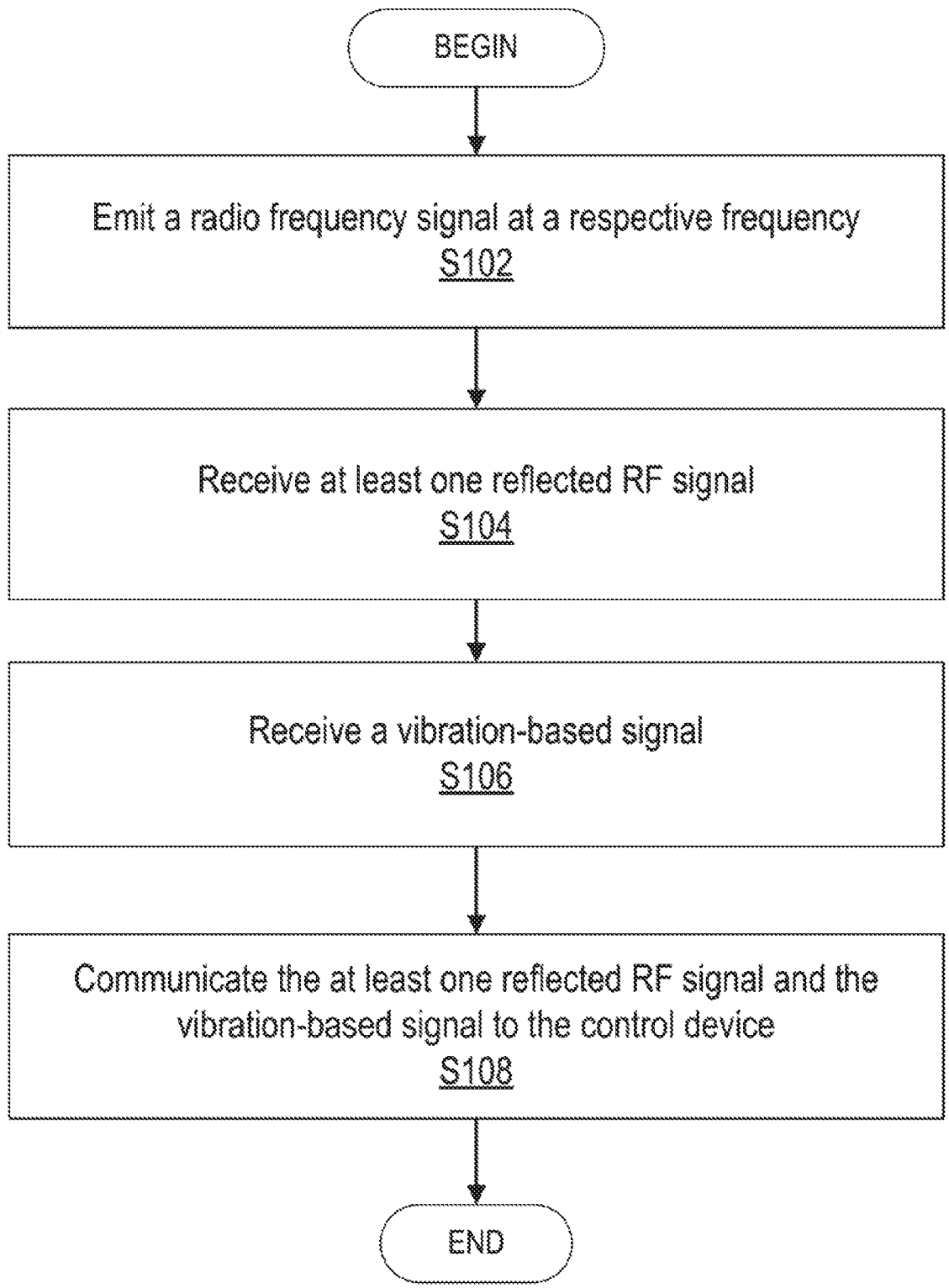
FIG. 4 is a flow diagram of an example process according to one or more embodiments of the disclosure.

FIG. 4 is an example flowchart of a process implemented by RF transceiver 14 according to one or more embodiments of the invention. One or more Blocks and/or functions performed by RF transceiver 14 may be performed by one or more elements of RF transceiver 14 such as by signal unit 46, processing circuitry 38, processor 40, etc. In one or more embodiments, RF transceiver 14 such as via one or more of signal unit 46, processing circuitry 38, processor 40, radio interface 36, etc. is configured to emit (Block S102) a radio frequency signal at a respective frequency, as described herein. In one or more embodiments, RF transceiver 14 such as via one or more of signal unit 46, processing circuitry 38, processor 40, radio interface 36, etc. is configured to receive (Block S104) at least one reflected RF signal, as described herein.

In one or more embodiments, RF transceiver 14 such as via one or more of signal unit 46, processing circuitry 38, processor 40, radio interface 36, etc. is configured to receive (Block S106) a vibration-based signal, as described herein. In one or more embodiments, RF transceiver 14 such as via one or more of signal unit 46, processing circuitry 38, processor 40, radio interface 36, etc. is configured to communicate (Block S108) the at least one reflected RF signal and the vibration-based signal to the control device 12, as described herein.

Having generally described arrangements for RF beacon 18 location monitoring, details for these arrangements, functions and processes are provided as follows, and which may be implemented by the control device 12 and/or RF transceiver 14.

Object Triangulation:

In one or more embodiments, signals radiated from RF transceiver 14 may be scattered from any material in the operating room, i.e., predefined area/environment, including the personnel performing the surgery. These scattered signals can be filtered out by looking at doppler offsets since RF beacons 18 may be configured to oscillate at specific frequencies which re-radiate the signals at known doppler offsets. In one or more embodiments, doppler filtering is configured to allow for the detection of weak signals in the presence of strong clutter by at least in part differentiating moving object signatures from static object signatures. An object signature may correspond to one or more transmitted and/or reflected by an object.

In one or more embodiments, three RF transceivers 14 are located around the region of interest, for example, bone tracking for orthopedic applications, and tool tracking, for example a bone saw or drill for surgical applications. In one or more embodiments, the three RF transceivers 14 emit waves at varying frequencies in cascading pulses of milliseconds, therefore each returning wave to the RF transceiver 14 may be from a different frequency.

In one or more embodiments, the RF transceivers 14 may be in a circular configuration, for example located on the light handle, and a fourth RF transceiver 14 for better triangulation of the RF beacons 18 may be used where RF beacons 18 may be removably inserted into pins. A method for tracking all three RF transceivers 14 with respect to each other, to generate a circular arc with 120 degrees of separation between the radars may be used. In one or more embodiments, a resistive wire with known resistance and a sinusoidal shape, when in tension, changes resistance, determining the circumference of the circle and hence the center of the circle the three RF transceivers 14 create to find object distance to the found circle center.

Control device 12 may be used to determine the sub millimeter differences affect each change in distance. In one or more embodiments, a laser range finder may be attached to the RF transceivers 14 to determine true distance from the radars prior to the surgery (referred to herein as preoperative, or preop calibration). Once the ranges are set, wavelengths of appropriate frequency for each RF transceiver 14 may be used for that range of distance to yield the readings for the tools and bones, which may help improve accuracy of the distance determination.

In one or more embodiments, Fourier transforms may be implemented by RF transceiver 14 such a via processing circuitry 38 and/or signal unit 46 to be used for each wave, i.e., RF signal, that is emitted from each RF transceiver 14 at varied time stamps and frequencies. For example, in one or more embodiments, the three sets of waves, RF signals, may be sent out in different time stamps with different frequencies where each wave packet with a combination of waves constitute the final waveform. The objects that return the wave such as a femoral, tibial, or tool RF beacon 18 may return waves, i.e., RF signals, that are distinctly different from the transmitted waves. Depending on the returned waves, inverse Fourier transform can be used such as by processing circuitry 38 and/or processing circuitry 26 to determine the missing wave type, and therefore, the tool associated with the missing wave type. In one or more embodiments, wave type may include one or more characteristics of the wave such as frequency, power, etc.

In one or more embodiments, RF transceivers 14 may trace their available field of vision with an arrayed approach with fixed vision. This means that the RF transceivers 14 such as via one or more of processing circuitry 38, signal unit 46, radio interface 36, etc. can sweep the area at a high frequency with constructive and destructive waves that couple. Once the RF transceivers 14 detects returned waves such as from RF beacon 18, the RF transceivers 14 may "lock" in on this region of interest (ROI) and sweep this area at a higher frequency, i.e., processing circuitry 38 reduces the field of vision for frequency sweeping. If the object associated with the RF beacon 18 moves out of this area as may be determined by processing circuitry 38 due to a lack of a detected return signal, the RF transceiver 14 may re-sweep the available field of vision to find the RF beacon 18 and corresponding object, and provide feedback to control device 12 if the object associated with an RF beacon 18 is not found. Further, in one or more embodiments, laser range finders can be utilized to improve the distance from radar to improve radar wavelength determination. Further, while system 10 is described as using three RF transceivers 14, the teachings herein are equally applicable to other quantity of RF transceivers such as less than 3 and/or greater than 3.

Example technique for using objection location:

After exposure for performing knee arthroplasty (total or partial), prior to scanning the bone, two screws may be placed in each bone, one in distal femur and one over proximal tibia. The pin is hollow and can accept RF beacon 18. Each RF beacon 18 may have an RFID device and a resonating feature and may have a QR code printed on the surface. This QR code can be customized based on patient's anatomy, choice of implant and surgeon's preference prior to surgery.

A 3D laser scanner may be used during surgery to scan the bony and cartilage surface, including the RF beacon 18. Radio Frequency Identifiers (RFID) are used to determine the unique part number of each pin and differentiate the pins in surgery. The code is recognized by the RF transceiver 14 and/or control device 12 and the pre-operative loaded library of joint images, preferences and implant sizes are loaded.

The scan may then uploaded to a cloud-based platform that is accessible by at least control device 12. The data is analyzed by, for example, AI/ML algorithm based on an automated script that identifies landmarks for the featured bone and bony/soft-tissue landmarks are identified. This scan may then be superimposed on pre-operative images, if available, for better registration process. A masking feature may be used to train the script to identify and better overlay the point clouds to each other with an RMS error minimizing algorithm.

While the scan is being analyzed, the patient's join may be put through range of motion, for example in knee, flexion and extension of the knee is assessed. Then the knee is subjected through manual varus/valgus tests to assess the soft tissue. The two RF beacons are tracked during this process by system 10 and the change in the distance is analyzed such as by control device 12 via processing circuitry 26 and/or location unit 16 as a change in the gaps during knee range of motion.

Cutting tools (i.e. objects) such as a bone saw or a cutting blocks that helps the surgeon make the cuts can be tracked during surgery by a third RF beacon 18 and placed in the appropriate location to achieve the planned surgery. Cutting devices may also have a RF beacon 18 and/or RF transceiver 14 attached to them to track and find landmarks that identify the location of cut planes or bone interaction locations to modify the surface.

Machine learning algorithms implemented, for example, by control device 12 and/or RF transceiver 14 are used to assess the optimum position of the implant based on prior patient outcomes. For example, patient types are clustered to individual specialized groups based on multiple parameters using regression analysis such as via processing circuitry 26. Control device 12 may identify the patient and find the best outcomes from previous surgeries performed on this patient type to prescribe the best cutting planes to replicate this outcome. Parameters of the implant alignment can be set pre-operatively to expedite this process.

Alternatively, the 3D scanner can be mounted over the cutting tools such as an oscillating saw or drill. The scanner can detect the already scanned surface through object recognition software and demonstrate the proposed cutting/drilling planes that are to be executed.

Alternatively, a universal cutting jig is used that accommodates for the tracking pin, i.e., pin with an RF beacon 18, as a fixed point. A manual jig that is tracked by the RF transceiver 14 and has a flat surface is positioned over the cutting block. The cutting block is now being tracked as compared to other tracking pins, i.e., with RF beacon 18, for both femur and tibia, separately, and pinned in place. The accurate position of the cutting block is shown on the monitor.

Alternatively, augmented reality while the surgeon is wearing a headset in communication with control device 12 is used to assess for accurate position of the cutting block or cutting plane of the saw.

Alternatively, a haptic robotic cutting tool can be used to execute the bony cuts.

After the cuts are made and trial implants are placed, knee is put through range of motion and stressed to assess soft-tissue tension and post-cut kinematic data. Artificial Intelligence implemented by control device 12, for example, is used to determine the landmarks and detect the axes of the bone based on prior cases.

The combination of artificial intelligence and machine learning software implemented in the cloud and/or control device 12 may eliminate the required advanced pre-operative imaging such as MRI or CT over time. X-rays can be used in adjunct to the intra-operative scan to determine the bone alignments.

The 3D scan and radar coordinates are relayed and stored in the cloud computing service in communication with control device 12 and/or stored at control device 12. The coordinates may be converted into machine learning algorithms, which are then used to build a mathematical model of training data. Every surgery builds a library of data and algorithms. These datasets may be continuously fed into the machine learning platform that may then cycle back to each, as described herein, such as identifying bony surfaces and generating cutting planes, tailored to the patient's unique soft tissue balance and alignment as well as surgeon's preference. The RF transceiver 14 can also be used to make measurements after the cuts to determine the accuracy of the cuts to report back to the surgeon to conduct validation.

Figure 5:
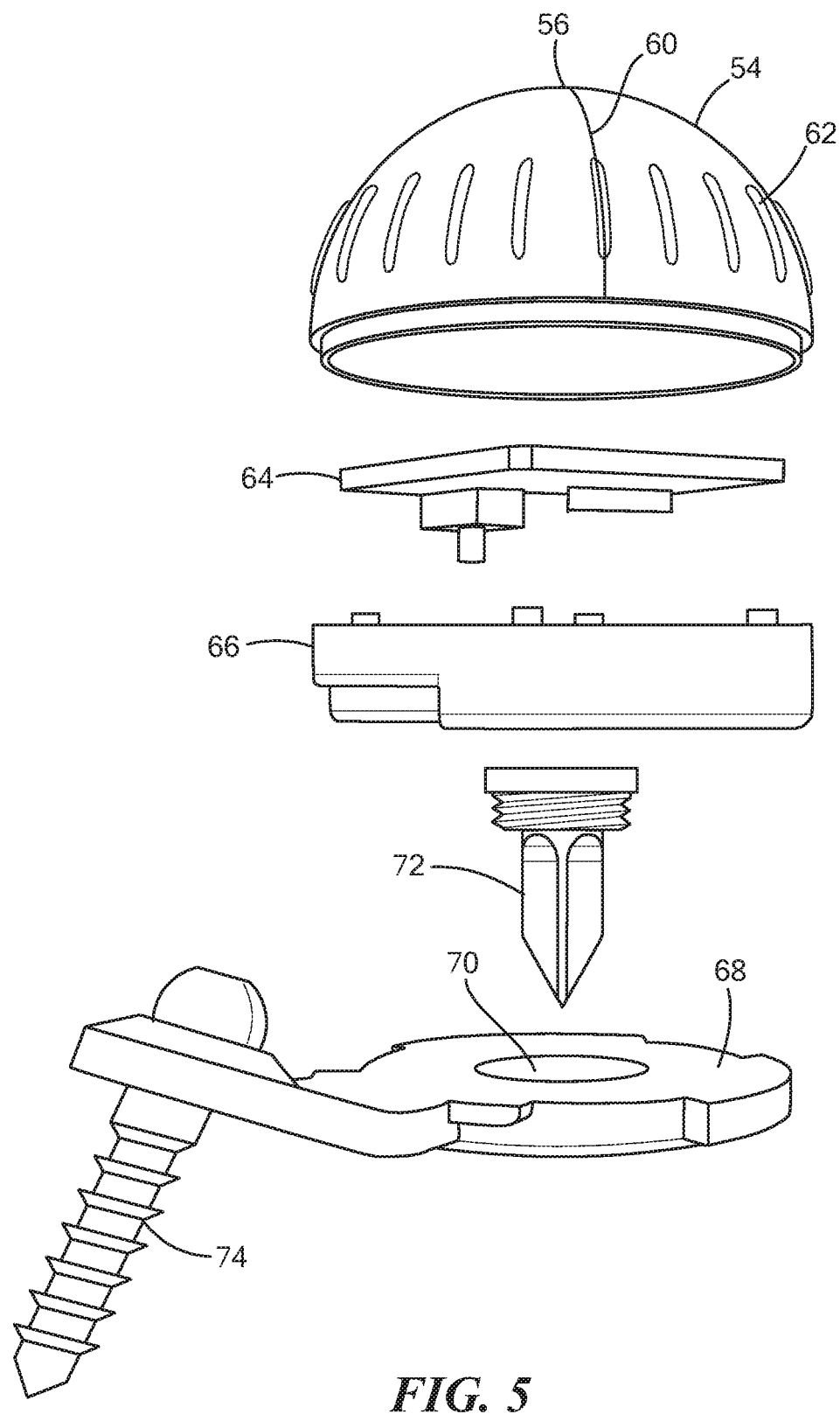
FIG. 5 is an exploded view of an exemplary beacon constructed according to one or more embodiments of the disclosure.
Figure 6:
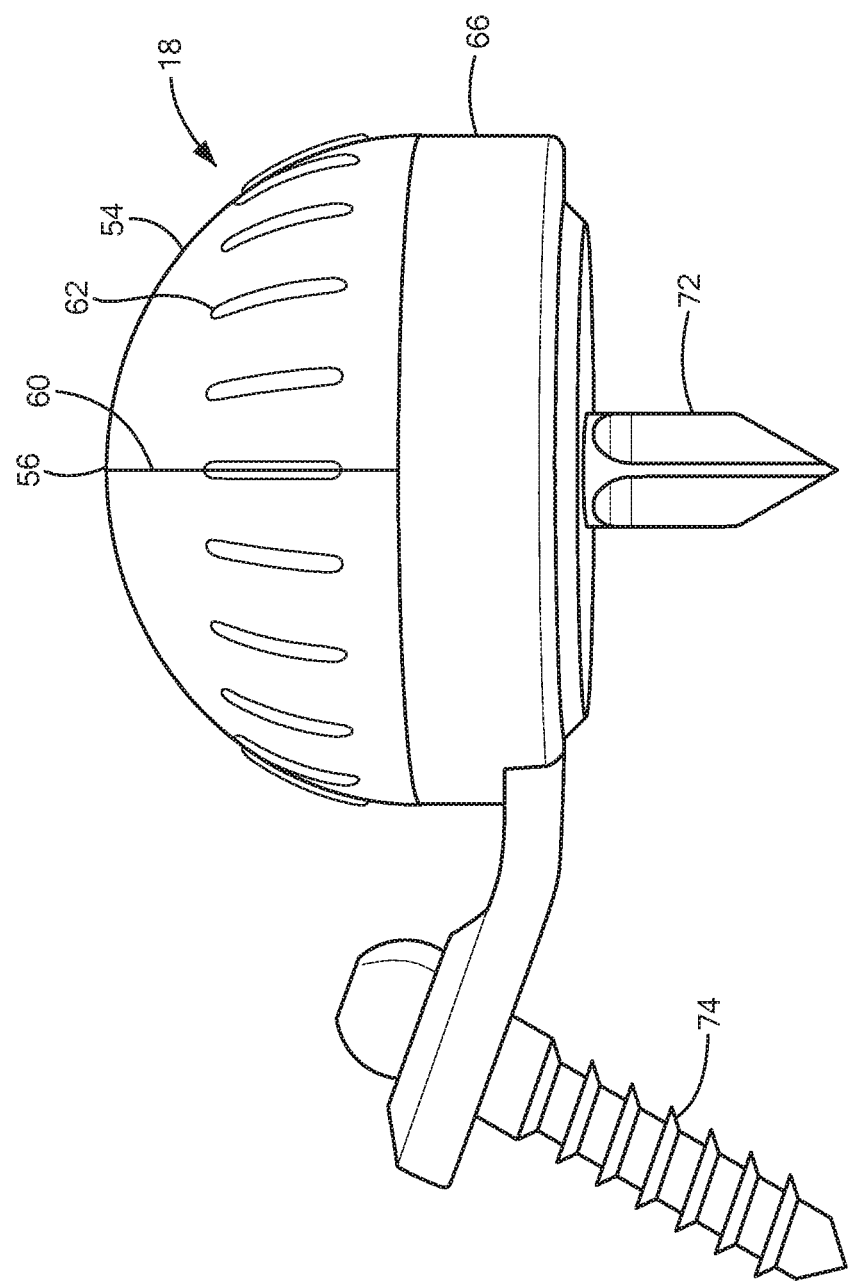
FIG. 6 is an assembled view of the beacon shown in FIG. 5.
Figure 7:
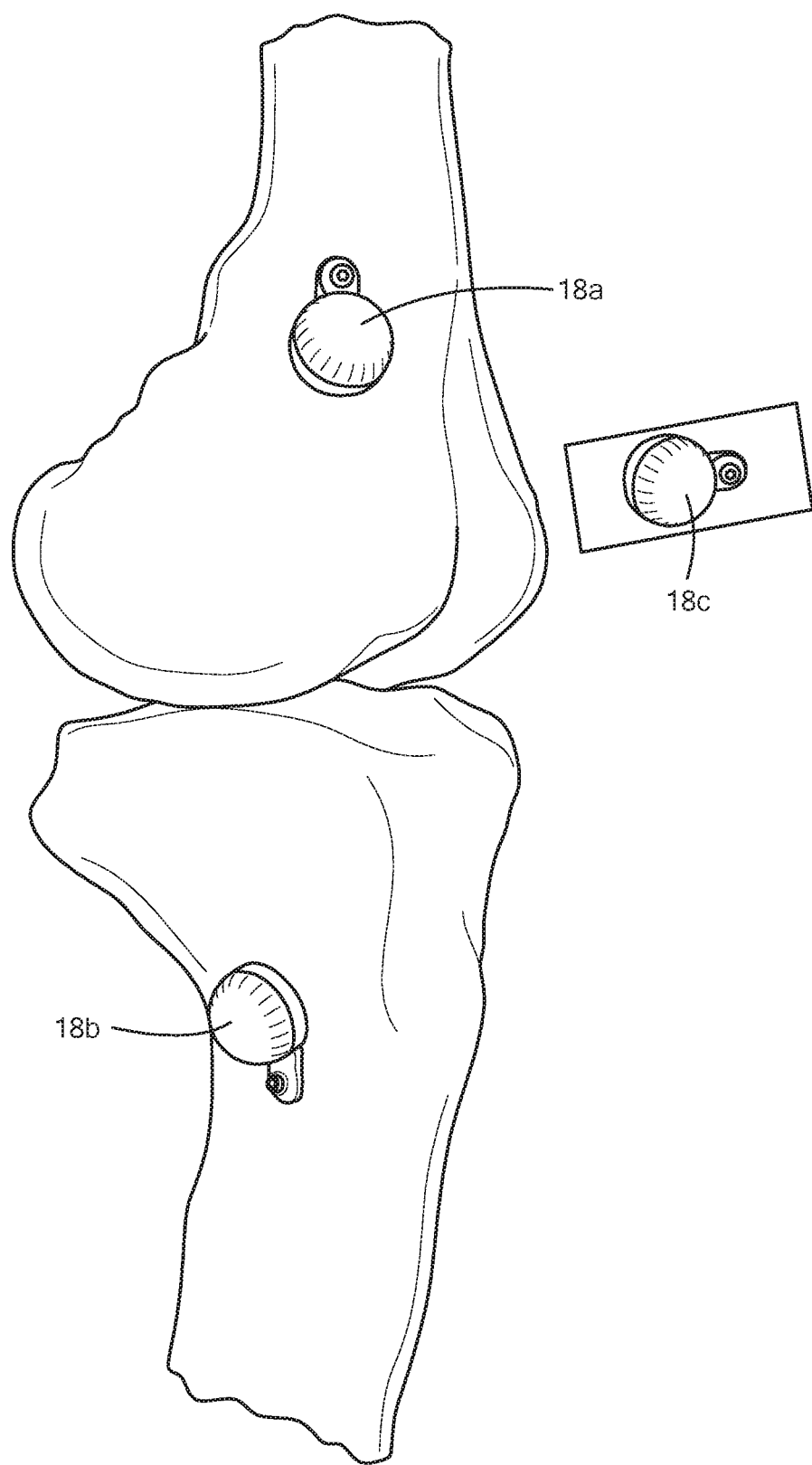
FIG. 7 is view showing three beacons mounted to medical objects, namely, the femur, the tibia, and a cutting element of robotic arm.

Referring now to FIGS. 5-7, RF beacons 18*a-n* may be sized and configured to be releasably attached to the medical object, for example, bone (shown in FIG. 7) or a cutting instrument of a robotic arm. For example, RF beacon 18*a* may be anchored to the distal end of the femur, RF beacon 18*b* may be anchored to the proximal end of the tibia, and RF beacon 18*c* may be anchored to the cutting instrument of the robotic arm. Each RF beacon 18 may include a dome 54 which, in one configuration, has a diameter of 1.5 cm. In other configurations, the diameter of the dome 54 may be 0.5 cm to 2 cm. The dome 54 includes an antenna 56 disposed therein and indicator line 60 may extend form the base of the dome 54 to the apex. A plurality of gripping elements 62 may be disposed around the circumference of the dome 54 to provide tactile feedback to the physician when the dome 54 is touched. Subjacent to the dome may be a circuit board 64, for example, a PCB which includes the electronics of the beacon 18. The circuit board 64 may include circuitry configured to cause a doppler shift in the received RF signal. For example, the circuitry is configured to actively modify the incoming first RF frequency and shift the frequency to a second RF frequency different than the first frequency without using vibration based signals discussed above. The frequency shift for each beacon 18 can be programmed such that each beacon 18 can shift the incoming frequency by a predetermined amount. Coupled to the circuit board 64 may be an antenna extending upward into the dome 54 and an accelerometer.

Continuing to refer to FIGS. 5-7, the circuit board 64 is sized to be received or otherwise coupled to a housing 66 which is coupled to the dome 54. In an exemplary configuration, the housing 66 defines a diameter commensurate in size with the maximum diameter of the dome. As shown in FIG. 6, the dome 54 is sized to coupled with the housing and to together with the housing to retain the circuit board 64 therein. Subjacent to housing 66 is a platform 68 sized and configured releasably mount the dome 54 and the housing 66. In an exemplary configuration, the housing 66 is configured to twist-lock with the platform 68, which may further align the apex of the dome 54 to be parallel with the axis of the platform 68. The platform 68 may further define an aperture 70 therethrough in which a first fixation element 72 may be disposed and extending orthogonally from the platform 68. The first fixation element 72 includes a plurality of threads to releasably attach to the platform 68 and may define a cross-shape extending from the threads to aid in the initial purchase of the bone. In particular, the cross shaped design facilitates initial rotational stability and penetration on the cortex of the bone. Extending at an oblique angle form the platform 68 and spaced a distance from the aperture is a second fixation element 74. In the configuration shown in FIGS. 6 and 7, the platform 68 has a tilt that accommodates for the curvature of the distal medial femur and proximal tibia. The second fixation element 74 facilitates overall stability of the platform 68.

In another embodiment, a wireless, radio frequency (RF) communicating device (e.g. Bluetooth, wifi) is utilized to achieve a 6 degree of freedom (DOF) tracking system where position and orientation of tracking is provided by a plurality of Inertial Measurement Unit (IMU) sensors (such as accelerometer, gyroscope and magnetometers). A secondary positional tracking source using radar signals will establish 3 DOF positions. Using the 3 DOF radar data will achieve the correct interpolation noise or drift errors from IMU based tracking. The secondary system can operate synchronously or asynchronously from a primary IMU based tracking system.

As will be appreciated by one of skill in the art, the concepts described herein may be embodied as a method, data processing system, computer program product and/or computer storage media storing an executable computer program. Accordingly, the concepts described herein may take the form of an entirely hardware embodiment, an entirely software embodiment or an embodiment combining software and hardware aspects all generally referred to herein as a "circuit" or "module." Any process, step, action and/or functionality described herein may be performed by, and/or associated to, a corresponding module, which may be implemented in software and/or firmware and/or hardware. Furthermore, the disclosure may take the form of a computer program product on a tangible computer usable storage medium having computer program code embodied in the medium that can be executed by a computer. Any suitable tangible computer readable medium may be utilized including hard disks, CD-ROMs, electronic storage devices, optical storage devices, or magnetic storage devices.

Some embodiments are described herein with reference to flowchart illustrations and/or block diagrams of methods, systems and computer program products. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer (to thereby create a special purpose computer), special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable memory or storage medium that can direct a computer or other programmable data processing apparatus to function in a particular manner, such that the instructions stored in the computer readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks.

It is to be understood that the functions/acts noted in the blocks may occur out of the order noted in the operational illustrations. For example, two blocks shown in succession may in fact be executed substantially concurrently or the blocks may sometimes be executed in the reverse order, depending upon the functionality/acts involved. Although some of the diagrams include arrows on communication paths to show a primary direction of communication, it is to be understood that communication may occur in the opposite direction to the depicted arrows.

Computer program code for carrying out operations of the concepts described herein may be written in an object-oriented programming language such as Java® or C++. However, the computer program code for carrying out operations of the disclosure may also be written in conventional procedural programming languages, such as the "C" programming language. The program code may execute entirely on the user's computer, partly on the user's computer, as a stand-alone software package, partly on the user's computer and partly on a remote computer or entirely on the remote computer. In the latter scenario, the remote computer may be connected to the user's computer through a local area network (LAN) or a wide area network (WAN), or the connection may be made to an external computer (for example, through the Internet using an Internet Service Provider).

Many different embodiments have been disclosed herein, in connection with the above description and the drawings. It will be understood that it would be unduly repetitious and obfuscating to literally describe and illustrate every combination and subcombination of these embodiments. Accordingly, all embodiments can be combined in any way and/or combination, and the present specification, including the drawings, shall be construed to constitute a complete written description of all combinations and subcombinations of the embodiments described herein, and of the manner and process of making and using them, and shall support claims to any such combination or subcombination.

It will be appreciated by persons skilled in the art that the embodiments described herein are not limited to what has been particularly shown and described herein above. In addition, unless mention was made above to the contrary, it should be noted that all of the accompanying drawings are not to scale. A variety of modifications and variations are possible in light of the above teachings.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A system for medical object tracking, comprising:
a plurality of radio frequency transceivers, each of the plurality of radio frequency transceivers configured to emit a radio frequency signal at a first respective frequency;
a plurality of radio frequency beacons, each of the plurality of radiofrequency beacons being removably attachable to a respective medical object, the respective medical object being one of a bone and a cutting instrument, each radio frequency beacon including:
a dome, the dome including an antenna disposed within;
a mounting;
a first medical object fixation element extending from and perpendicular to the mounting;
a second medical object fixation element being disposed at an oblique angle to the mounting; and
at least one inertial measurement unit (IMU) sensor disposed within the dome;
processing circuitry disposed between the dome and the mounting, the at least one IMU sensor and the antenna being affixed to the processing circuitry;
wherein the processing circuitry is configured to obtain a modified radio signal by modifying the radio frequency signal from the respective first frequency to a second respective frequency different than the first respective frequency; and
a control device in communication with the plurality of radio frequency transceivers, the control device including processing circuitry configured to determine a location of the respective medical object in three-dimensional space based at least in part on the modified radio frequency signal.

2. The system according to claim 1, wherein the plurality of radio frequency beacons includes three beacons, a first of the plurality of beacons being configured to be removably affixed to the distal end of a femur, a second of the plurality of beacons being configured to be removably affixed to a proximal end of a tibia, and a third of the plurality of beacons being configured to be removably affixed to a cutting instrument of a robotic arm.

3. The system of claim 1, wherein the control device is configured to measure one or more of a tilt and positional data to obtain a six-degree-of-freedom measurement based on information from the IMU and/or two or more of the plurality of radio frequency beacons.

4. The system of claim 3, wherein each radio frequency beacon of the plurality of radio frequency beacons comprises an accelerometer configured to measure one or more of a pitch, a roll, and a yaw of the radio frequency beacon.

5. The system of claim 4, wherein data from the accelerometer is transmitted wirelessly to the control device.

6. The system of claim 1, wherein the processing circuitry operates asynchronously from the control device.

7. The system of claim 1, wherein the first medical object fixation element comprises a pin.

8. The system of claim 1, wherein the plurality of radio frequency transceivers are arranged in a substantially circular configuration.

9. The system of claim 1, wherein the system is pre-calibrated based on one or more frequency generating devices external to the system, each of the one or more frequency generating devices producing a unique signal signature, and wherein software executed by the control device is configured to filter each unique signal signature and assign a unique frequency to a respective beacon based on a detected unique signal signature.

10. The system of claim 1, wherein the antenna housing and processing circuitry are releasably attached to the mounting.

11. A system for medical object tracking, comprising:
a plurality of radio frequency transceivers, each of the plurality of radio frequency transceivers configured to emit a radio frequency signal at a first respective frequency;
a plurality of radio frequency beacons, each of the plurality of radiofrequency beacons being removably attachable to a respective medical object, the respective medical object being one of a bone and a cutting instrument, each radio frequency beacon including:
a mounting;
a first medical object fixation element extending from and perpendicular to the mounting;
a second medical object fixation element being disposed at an oblique angle to the mounting;
an antenna housing, the antenna housing including an antenna disposed within;
at least one inertial measurement unit (IMU) sensor disposed within the antenna housing;
processing circuitry disposed between the antenna housing and the mounting, the at least one IMU sensor and the antenna being affixed to the processing circuitry; and
the processing circuitry being configured to obtain a modified radio frequency signal by modifying the radio frequency signal from the respective first frequency to a second respective frequency different than the first respective frequency; and
a control device in communication with the plurality of radio frequency transceivers, the control device including processing circuitry configured to determine a location of the respective medical object in three-dimensional space based at least in part on the modified radio frequency signal.

12. The system of claim 11, wherein the control device is configured to measure one or more of a tilt and positional data to obtain a six-degree-of-freedom measurement based on information from the IMU and/or two or more of the plurality of radio frequency beacons.

13. The system of claim 12, wherein each radio frequency beacon of the plurality of radio frequency beacons comprises an accelerometer configured to measure one or more of a pitch, a roll, and a yaw of the radio frequency beacon.

14. The system of claim 13, wherein data from the accelerometer is transmitted wirelessly to the control device.

15. The system of claim 11, wherein the processing circuitry operates asynchronously from the control device.

16. The system of claim 11, wherein the first medical object fixation element comprises a pin.

17. The system of claim 11, wherein the plurality of radio frequency transceivers are arranged in a substantially circular configuration.

18. The system of claim 11, wherein the system is pre-calibrated based on one or more frequency generating devices external to the system, each of the one or more frequency generating devices producing a unique signal signature, and wherein software executed by the control device is configured to filter each unique signal signature and assign a unique frequency to a respective radio frequency beacon based on a detected unique signal signature.

19. The system according to claim 11, wherein the plurality of radio frequency beacons includes three beacons, a first of the plurality of beacons being configured to be removably affixed to the distal end of a femur, a second of the plurality of beacons being configured to be removably affixed to a proximal end of a tibia, and a third of the plurality of beacons being configured to be removably affixed to a cutting instrument of a robotic arm.

* * * * *